(12) United States Patent
Min

(10) Patent No.: US 8,301,249 B2
(45) Date of Patent: Oct. 30, 2012

(54) SYSTEMS AND METHODS FOR EXPLOITING THE TIP OR RING CONDUCTOR OF AN IMPLANTABLE MEDICAL DEVICE LEAD DURING AN MRI TO REDUCE LEAD HEATING AND THE RISKS OF MRI-INDUCED STIMULATION

(75) Inventor: Xiaoyi Min, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 394 days.

(21) Appl. No.: 12/257,263

(22) Filed: Oct. 23, 2008

(65) Prior Publication Data

US 2010/0106214 A1    Apr. 29, 2010

(51) Int. Cl.
*A61N 1/00* (2006.01)
(52) U.S. Cl. ............. 607/9; 607/116; 607/119; 607/122
(58) Field of Classification Search ............... 607/9, 116, 607/119, 122
See application file for complete search history.

(56) References Cited

U.S. PATENT DOCUMENTS

| | | | |
|---|---|---|---|
| 4,437,474 A | 3/1984 | Peers-Trevarton | |
| 4,746,864 A | 5/1988 | Satoh | |
| 5,044,375 A | 9/1991 | Bach, Jr. et al. | |
| 5,063,348 A | 11/1991 | Kuhara et al. | |
| 5,197,468 A | 3/1993 | Proctor et al. | |
| 5,217,010 A | 6/1993 | Tsitlik et al. | |
| 5,306,291 A | 4/1994 | Kroll et al. | |
| 5,851,226 A * | 12/1998 | Skubitz et al. | 607/126 |
| 6,101,417 A | 8/2000 | Vogel et al. | |
| 6,161,040 A | 12/2000 | Blunsden | |
| 6,198,972 B1 | 3/2001 | Hartlaub et al. | |
| 6,871,091 B2 | 3/2005 | Wilkinson et al. | |
| 6,925,328 B2 | 8/2005 | Foster et al. | |
| 6,930,242 B1 | 8/2005 | Helfer et al. | |
| 6,944,489 B2 | 9/2005 | Zeijlemaker et al. | |
| 6,971,391 B1 | 12/2005 | Wang et al. | |
| 6,985,775 B2 | 1/2006 | Reinke et al. | |
| 7,050,855 B2 | 5/2006 | Zeijlemaker et al. | |

(Continued)

FOREIGN PATENT DOCUMENTS

WO    03037424 A2    5/2003

(Continued)

OTHER PUBLICATIONS

NonFinal OA (Restriction), mailed Jan. 12, 2011—Child U.S. Appl. No. 12/891,602.

(Continued)

*Primary Examiner* — Nicole F Lavert

(57) ABSTRACT

Systems and methods are provided for reducing heating within pacing/sensing leads of a pacemaker or implantable cardioverter-defibrillator that occurs due to induced radio frequency (RF) currents during a magnetic resonance imaging (MRI) procedure, or in the presence of other sources of strong RF fields. For example, bipolar coaxial leads are described wherein the ring conductor of the lead is disconnected from the ring electrode via a switch in response to detection of MRI fields to convert the ring conductor into an RF shield for shielding the inner tip conductor of the lead so as to reduce the strength of RF currents induced therein and hence reduce tip heating. Other exemplary leads are described wherein a band stop filter is instead used to block RF signals to likewise convert the ring conductor into an RF shield. The switches and band stop filters also help to prevent MRI-induced stimulation.

12 Claims, 11 Drawing Sheets

U.S. PATENT DOCUMENTS

| | | | |
|---|---|---|---|
| 7,164,950 B2 | 1/2007 | Kroll et al. | |
| 7,369,898 B1 | 5/2008 | Kroll et al. | |
| 7,729,770 B2 | 6/2010 | Cabelka et al. | |
| 2003/0013948 A1 | 1/2003 | Russell | |
| 2003/0083723 A1 | 5/2003 | Wilkinson et al. | |
| 2003/0083726 A1* | 5/2003 | Zeijlemaker et al. | 607/122 |
| 2003/0144716 A1 | 7/2003 | Reinke et al. | |
| 2003/0144718 A1 | 7/2003 | Zeijlemaker | |
| 2003/0144719 A1 | 7/2003 | Zeijlemaker | |
| 2004/0088012 A1 | 5/2004 | Kroll et al. | |
| 2006/0085043 A1 | 4/2006 | Stevenson | |
| 2007/0088416 A1 | 4/2007 | Atalar et al. | |
| 2008/0243218 A1 | 10/2008 | Bottomley et al. | |
| 2008/0262584 A1 | 10/2008 | Bottomley et al. | |

FOREIGN PATENT DOCUMENTS

| | | |
|---|---|---|
| WO | 03063946 A2 | 8/2003 |
| WO | 03063946 A3 | 8/2003 |
| WO | 03063946 C1 | 8/2003 |
| WO | 03063953 A2 | 8/2003 |
| WO | 03063953 A3 | 8/2003 |
| WO | 03037424 A3 | 5/2005 |

OTHER PUBLICATIONS

NonFinal Office Action, mailed Apr. 14, 2011—Child U.S. Appl. No. 12/891,602.

NonFinal Office Action, mailed Apr. 13, 2011—Related U.S. Appl. No. 12/257,245.

NonFinal Office Action, mailed Apr. 1, 2011—Related U.S. Appl. No. 12/042,605.

Final Office Action, mailed Aug. 10, 2011—Related U.S. Appl. No. 12/042,605.

\* cited by examiner

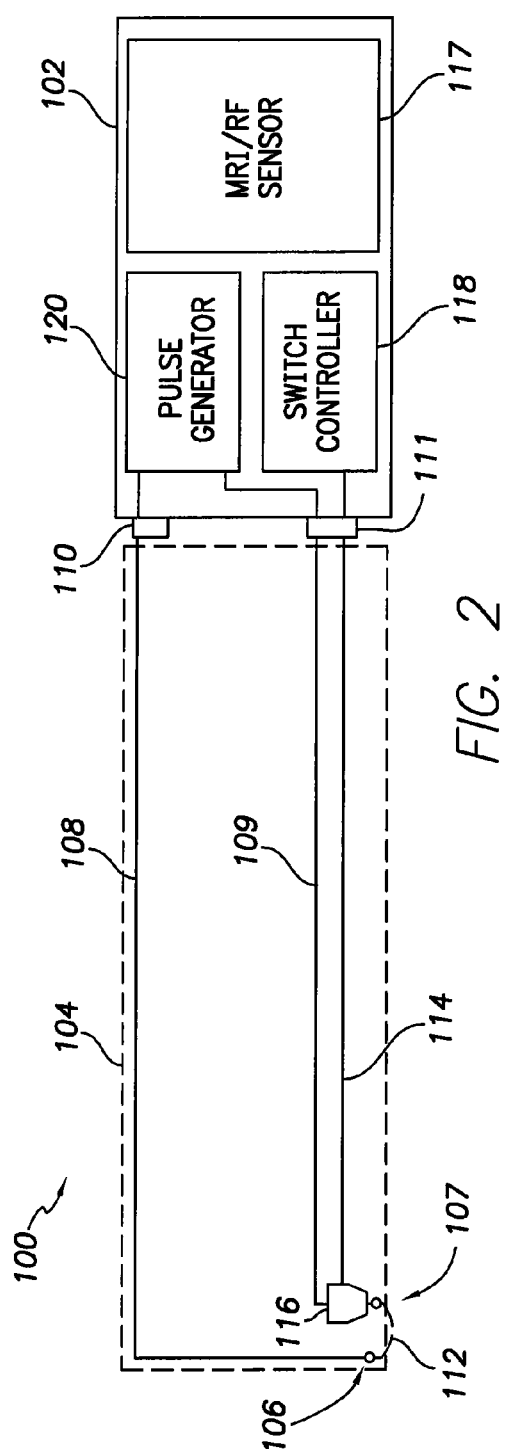
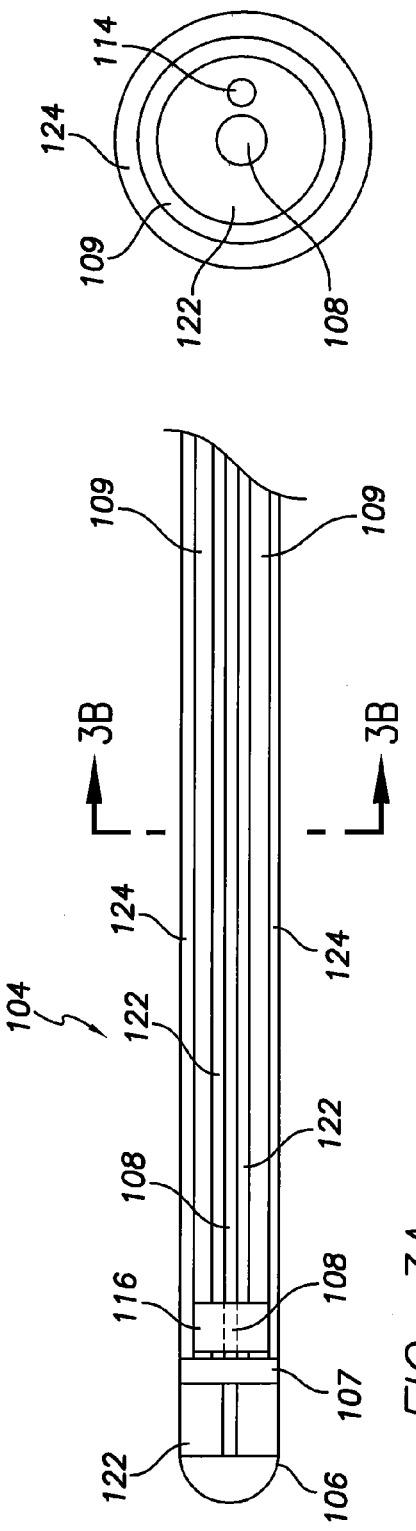
FIG. 2
FIG. 3A
FIG. 3B

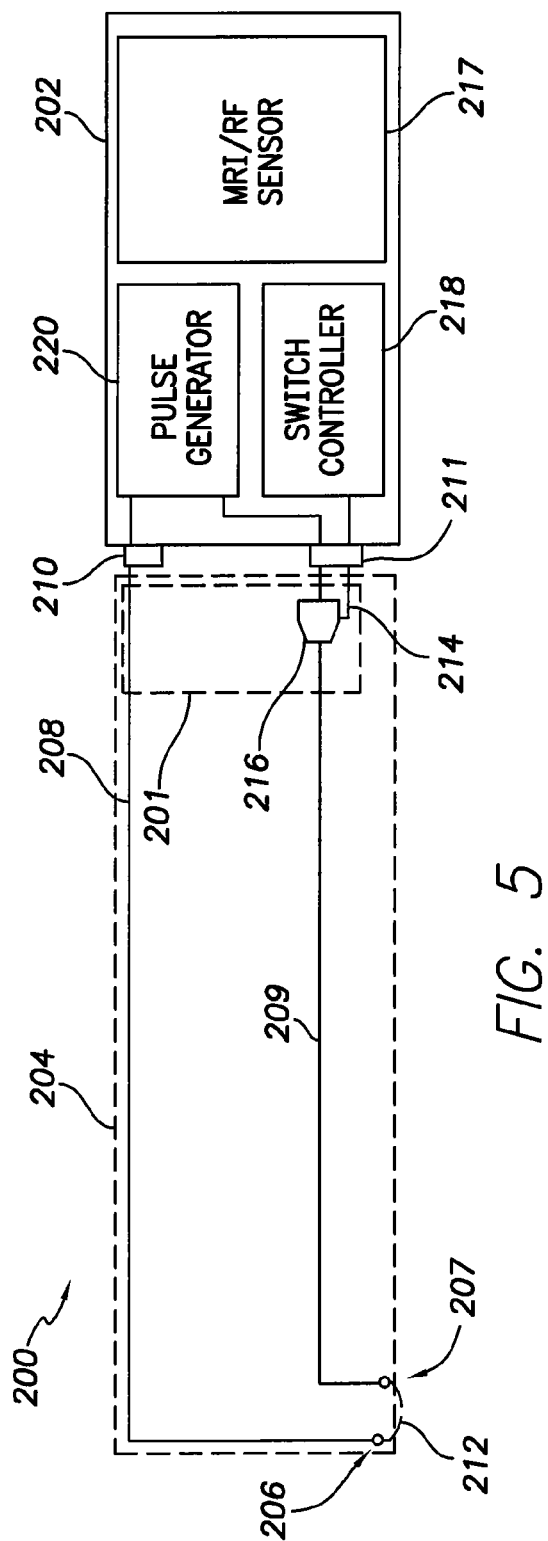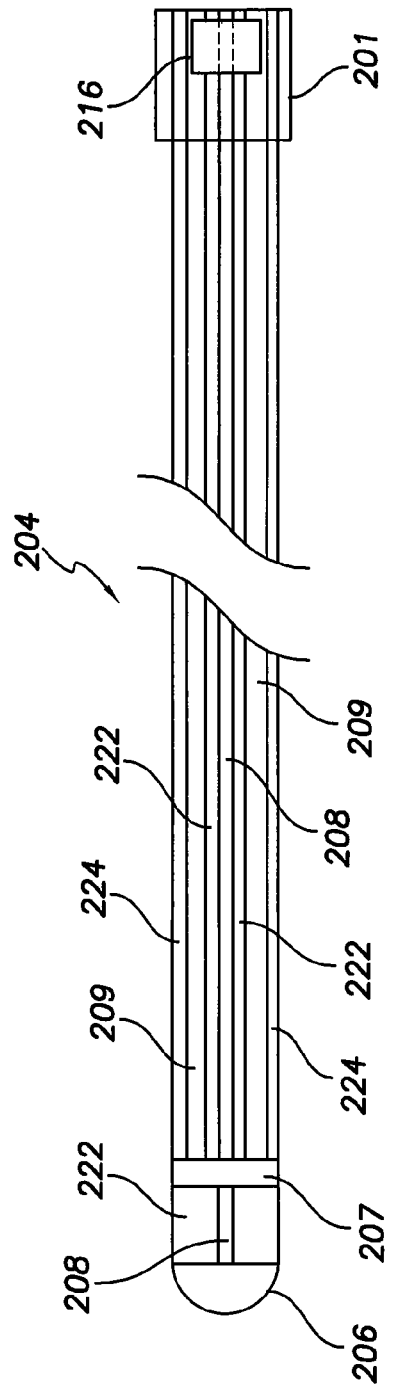

SYSTEMS AND METHODS FOR EXPLOITING THE TIP OR RING CONDUCTOR OF AN IMPLANTABLE MEDICAL DEVICE LEAD DURING AN MRI TO REDUCE LEAD HEATING AND THE RISKS OF MRI-INDUCED STIMULATION

CROSS-REFERENCE TO RELATED APPLICATIONS

This application is related to U.S. patent application Ser. No. 12/257,245, filed Oct. 23, 2008, entitled "Systems and Methods for Disconnecting Electrodes of Leads of Implantable Medical Devices During an MRI to Reduce Lead Heating."

FIELD OF THE INVENTION

The invention generally relates to leads for use with implantable medical devices, such as pacemakers or implantable cardioverter-defibrillators (ICDs), and to techniques for reducing tip heating within such leads during a magnetic resonance imaging (MRI) procedure.

BACKGROUND OF THE INVENTION

MRI is an effective, non-invasive magnetic imaging technique for generating sharp images of the internal anatomy of the human body, which provides an efficient means for diagnosing disorders such as neurological and cardiac abnormalities and for spotting tumors and the like. Briefly, the patient is placed within the center of a large superconducting magnet that generates a powerful static magnetic field. The static magnetic field causes protons within tissues of the body to align with an axis of the static field. A pulsed radio-frequency (RF) magnetic field is then applied causing the protons to begin to precess around the axis of the static field. Pulsed gradient magnetic fields are then applied to cause the protons within selected locations of the body to emit RF signals, which are detected by sensors of the MRI system. Based on the RF signals emitted by the protons, the MRI system then generates a precise image of the selected locations of the body, typically image slices of organs of interest.

However, MRI procedures are problematic for patients with implantable medical devices such as pacemakers and ICDs. A significant problem is that the strong fields of the MRI can induce currents within the lead system that cause the electrodes of leads of the implantable device to become significantly heated, potentially damaging adjacent tissues or the lead itself. Heating is principally due to the RF components of the MRI fields. In worst-case scenarios, the temperature at the tip of an implanted lead can increase as much as 70 degrees Celsius (C.) during an MRI. Although such a dramatic increase is probably unlikely within a system wherein leads are properly implanted, even a temperature increase of only about 8°-13° C. can cause myocardial tissue damage. Furthermore, any significant heating of the electrodes of pacemaker and ICD leads, particular tip electrodes, can affect pacing and sensing parameters associated with the tissue near the electrode, thus potentially preventing pacing pulses from being properly captured within the heart of the patient and/or preventing intrinsic electrical events from being properly sensed by the device. The latter may potentially result, depending upon the circumstances, in therapy being improperly delivered or improperly withheld. Another significant concern is that any currents induced in the lead system can potentially generate voltages within cardiac tissue comparable in amplitude and duration to stimulation pulses and hence might trigger unwanted contractions of heart tissue. The rate of such contractions can be extremely high, posing significant clinical risks on patients.

Hence, there is a need to reduce heating in the leads of implantable medical devices, especially pacemakers and ICDs, and to also reduce the risks of improper tissue stimulation during an MRI, which is referred to herein as MRI-induced pacing.

Various techniques have been developed to address these problems. See, for example, the following patents and patent applications: U.S. Pat. Nos. 6,871,091; 6,930,242; 6,944,489; 6,971,391 6,985,775; 7,050,855; 7,164,950; 7,489,495; U.S. Patent Application Nos. 2003/0144718, now abandoned, and 2003/0144719, now abandoned; as well as the following PCT documents WO03/037424, WO03/063946, WO03/063953. At least some of these techniques are directed to detecting MRI fields and to electrically disconnecting electrodes from the implantable device in an effort to prevent current loops from being generated that might induce lead heating, particularly tip heating. See, also, U.S. Pat. No. 7,369,898 to Kroll et al., entitled "System and Method for Responding to Pulsed Gradient Magnetic Fields using an Implantable Medical Device."

Various aspects of the invention are directed to providing MRI-based lead switching or band stop filtering systems and methods.

SUMMARY OF THE INVENTION

In accordance with various exemplary embodiments of the invention, a lead is provided for use with an implantable medical devices for implant within a patient wherein the lead includes first and second electrodes for placement adjacent patient tissues, a inner conductor for routing signals along the lead between the first electrode and the implantable medical device, and an outer conductor for routing signals along the lead between the second electrode and the implantable medical device. An insulator is interposed between the outer conductor and patient tissues. An electrical device is connected along the outer conductor between the second electrode and the implantable medical device, which is operative to selectively control the conduction of signals along the outer conductor in response to the presence of particular electromagnetic fields, such as the fields associated with MRIs to selectively convert the outer conductor into an electromagnetic signal shield to, e.g., shield the inner conductor during an MRI.

In one example, the electrical device is a switch connected along the outer conductor between the second electrode and the implantable medical device and operative to be selectively opened in response to the presence of MRI fields and closed otherwise. In one particular coaxial embodiment described herein, the ring conductor is the outer conductor of a pair of coaxial conductors within the lead. The tip conductor is the inner conductor of the pair. By disconnecting the ring electrode from ring conductor (and hence from tissues electrically coupled to the ring electrode) using the switch, the ring conductor thereby provides RF shielding to help prevent currents from being induced along the tip conductor by the MRI fields and to also prevent heating from ring electrode, particularly by the pulsed RF components thereof. Moreover, by disconnecting the ring electrode from the ring conductor, induced current loops are thereby also substantially prevented from arising along the ring conductor, thus further reducing the risk of undue lead heating on both tip and ring electrodes, as well as the risk of MRI-induced stimulation.

In another example, the electrical device is a band stop filter connected along the outer conductor between the second electrode and the implantable medical device, which is operative to be selectively block signals having frequencies associated with MRI fields. The band stop filter has the effect of disconnecting the ring electrode from the ring conductor at MRI frequencies so as to achieve similar advantages as with the switch. In this regard, a band stop filter exhibits high impedance near RF frequencies while allowing pacing and sensing signals to pass in the low frequency range. The band stop filter may be designed to provide single or multiple self-resonant frequencies at RF frequencies. Self-resonant inductors can be used for single or multiple resonant frequencies. Inductors and capacitors in parallel circuits as resonators can be also used.

In one particular example, the switch or a band stop filter is connected at the distal end of the ring conductor between the ring electrode and the ring conductor, thereby converting the ring conductor to an RF shield for the tip conductor during the MRI. In another example, the switch or a band stop filter is instead connected at the proximal end of the ring conductor within a header of the lead, again converting the ring conductor to an RF shield for the tip conductor during the MRI. In still other examples, the switch or a band stop filter is instead mounted along a ring terminal interconnect feed-through point of the implantable medical device. Multiple switches or band stop filters may be provided for use with the ring conductor. For example, one switch or band stop filter may be provided within the lead at the distal end of the ring conductor, while another switch or band stop filter may be provided within the feed-through of the implantable medical device. Still further, additional switches or filters may be provided along the tip conductor of the lead at various locations. That is, in addition to the use of a switch or band stop filter along the outer (ring) conductor, switches or filters can also be used along the inner (tip) conductor. Additional electrodes, coils and/or sensors may be positioned along the lead as well. Multiple leads may be employed.

The implantable medical device, which may be, e.g., a pacemaker or ICD, preferably includes a magnetometer or other magnetic field sensing device. Switching circuitry is provided within the device for opening the switches during an MRI and for closing the switches otherwise, so as to allow routine pacing/sensing operations while no MRI fields are present. In implementations wherein one or more switches are provided along the lead, suitable control signal lines are provided within the lead for allowing the implantable medical device to control the switches. The RF shielding techniques are particularly well suited for use with bipolar cardiac pacing/sensing leads for use with pacemakers and ICDs but may also be employed in connection with other implantable leads for use with other implantable medical devices. Moreover, the techniques may also be exploited within multi-polar coaxial leads, multi-lumen leads. For multi-polar leads, the aforementioned switches or filters are preferably connected along the outermost conductor of the lead so that the outermost conductor can then providing RF shielding to any internal conductors.

BRIEF DESCRIPTION OF THE DRAWINGS

The above and further features, advantages and benefits of the invention will be apparent upon consideration of the descriptions herein taken in conjunction with the accompanying drawings, in which:

FIG. 2 is a block diagram, partly in schematic form, illustrating a bipolar lead for use with the pacer/ICD of FIG. 1 wherein a switching element is mounted to the lead near the ring electrode, and also illustrating a pacer/ICD connected to the lead having an MRI-responsive switch controller;

FIG. 3 is an elevation view of a portion of the bipolar lead of FIG. 2 and also a cross-sectional view;

FIG. 5 is an elevational view of a portion of an alternative bipolar lead to that of FIG. 2, particularly illustrating the placement of a ring electrode switching element in the header of the lead;

FIG. 6 includes another elevation view of a portion of the bipolar lead of FIG. 5;

DETAILED DESCRIPTION OF THE PREFERRED EMBODIMENTS

The following description includes the best mode presently contemplated for practicing the invention. The description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of MRI System

Figure 1:
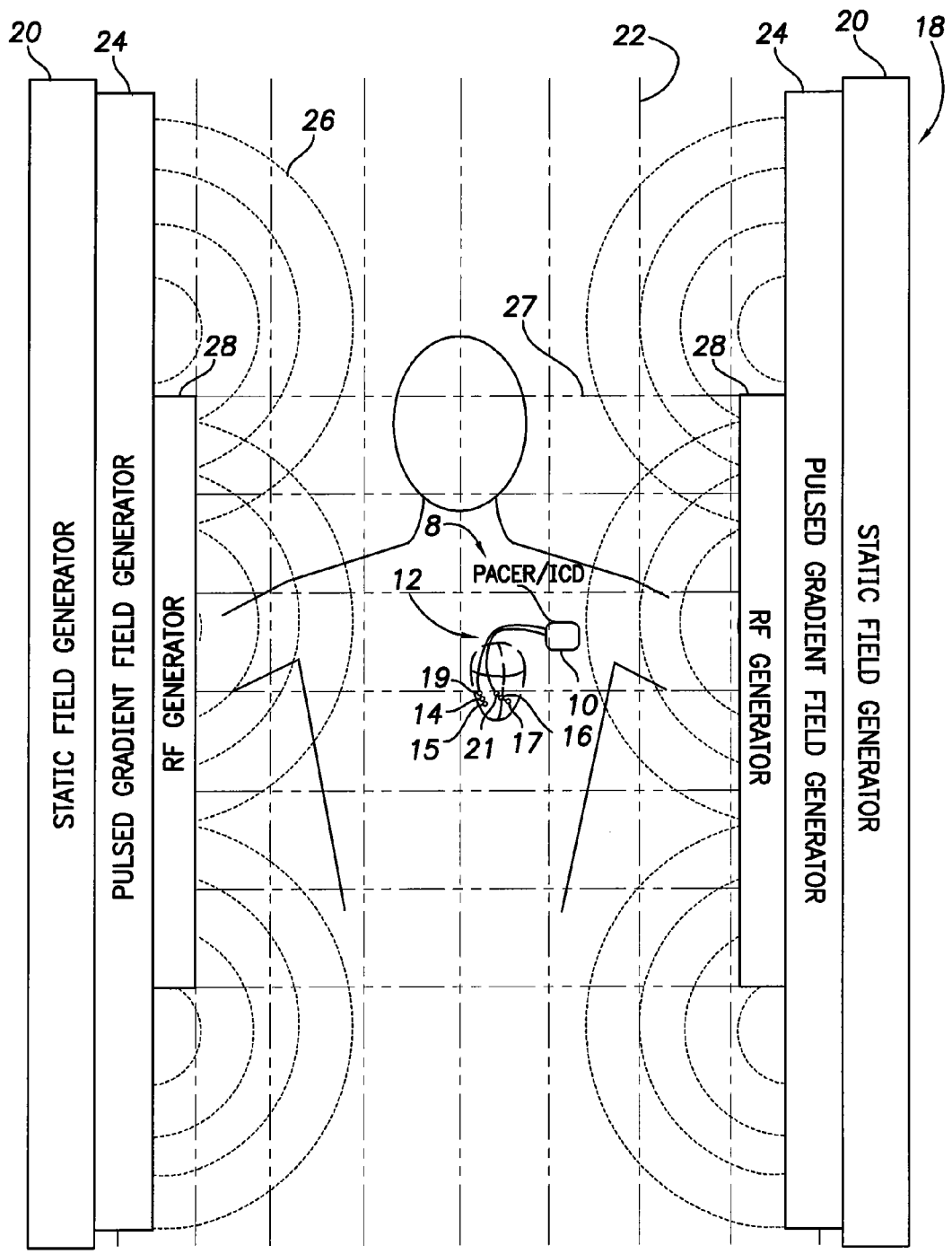
FIG. 1 is a stylized representation of an MRI system along with a patient with a pacer/ICD implanted therein with leads employing ring electrode switching elements.
Figure 12:
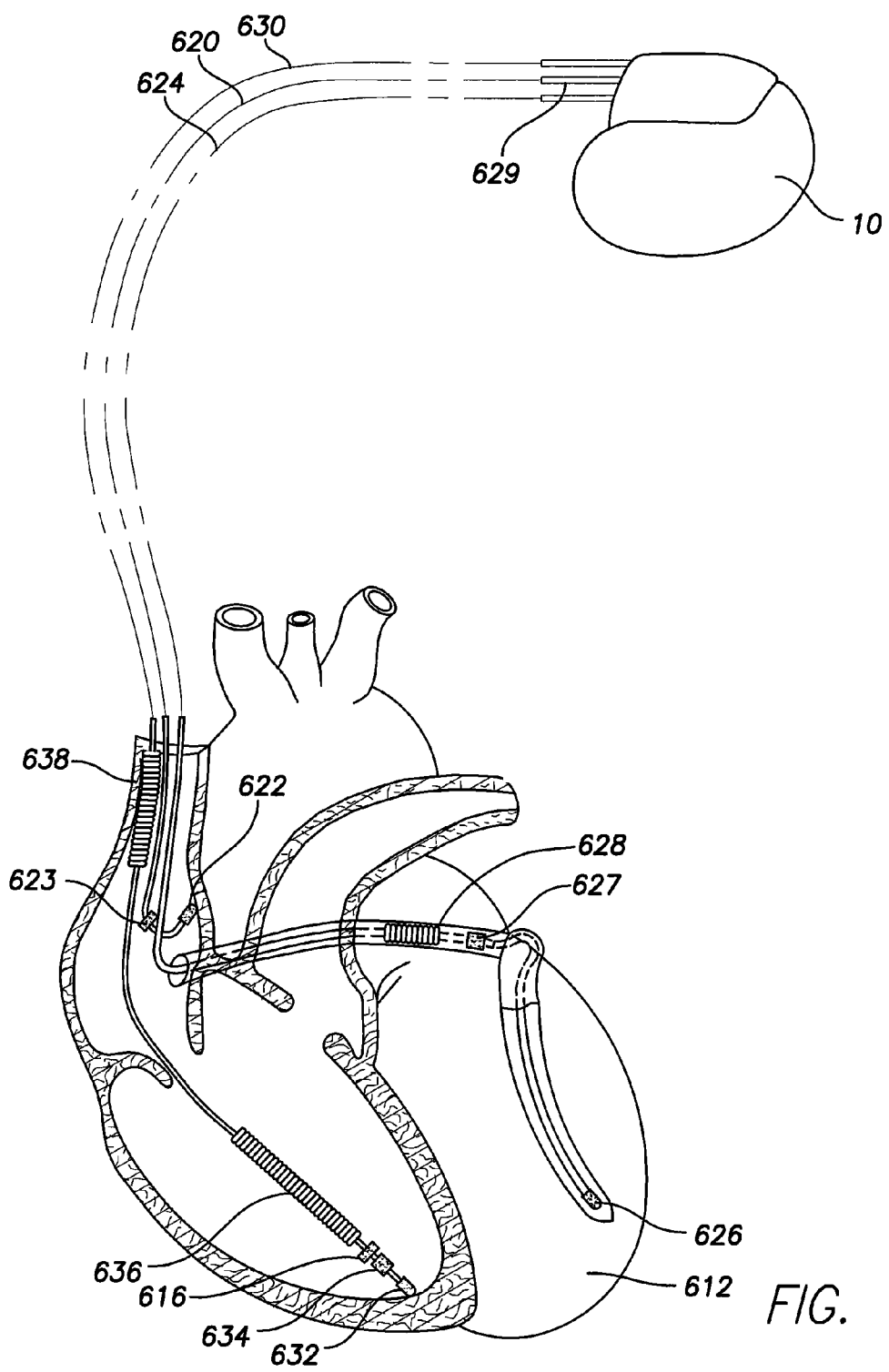
FIG. 12 is a simplified, partly cutaway view, illustrating the pacer/ICD of FIG. 1 along with a more complete set of leads implanted in the heart of the patient, wherein the RV lead includes a switching or filter element near the location of the ring electrode.

FIG. 1 illustrates an implantable medical system 8 having a pacer/ICD 10 for use with a set of coaxial bipolar pacing/sensing leads 12, which include tip and ring electrodes 14, 15, 16 and 17, as well as ring electrode switching elements 19 and 21. Switching circuitry within the pacer/ICD is operative to control the ring switches to electrically disconnect the ring electrodes from the pacing/ICD in the presence of MRI fields to reduce lead heating caused by magnetic fields generated by an MRI system 18. This is achieved, at least in part, by converting outer ring conductors of the leads (not separately shown within FIG. 1) into RF shields for shielding portions of inner tip conductors of the leads (also not separately shown in FIG. 1). In FIG. 1, only two leads are shown, a right ventricular (RV) lead and a left ventricular (LV) lead. A more complete lead system is illustrated in FIG. 12, described below. As will be explained further, ring electrode switching elements may instead be positioned elsewhere along the lead, such as in the header of the lead, or may be positioned within the pacer/ICD itself, such as within the feed-through of the pacer/ICD. In some implementations, multiple switching elements may be provided per lead, including additional tip electrode switching elements.

As to the MRI system 18, the system includes a static field generator 20 for generating a static magnetic field 22 and a pulsed gradient field generator 24 for selectively generating pulsed gradient magnetic fields 26. The MRI system also includes an RF generator 28 for generating pulsed RF fields 27. Other components of the MRI, such as its sensing and imaging components are not shown either. MRI systems and imaging techniques are well known and will not be described in detail herein. For exemplary MRI systems see, for example, U.S. Pat. No. 5,063,348 to Kuhara et al., entitled "Magnetic Resonance Imaging System" and U.S. Pat. No. 4,746,864 to Satoh, entitled "Magnetic Resonance Imaging System." Note that the fields shown in FIG. 1 are stylized representations of the MRI fields intended merely to illustrate the presence of the fields. Actual MRI fields generally have far more complex patterns.

Thus, pacer/ICD 10 is equipped to detect the presence of the MRI fields and to open the ring switching elements 19, 21 so as to disconnect the ring electrodes 16, 16 from their respective outer ring conductors and from the pacer/ICD itself. This prevents current loops from being induced along the ring conductors through the ring terminals so as to reduce ring heating. Also, as noted, disconnecting the ring electrodes from the ring conductors converts the ring conductors into RF shields for shielding portions of the inner tip conductors of the coaxial leads so as to reduce the intensity of induced currents through the tip electrode so as to reduce tip heating. Other advantages may be afforded as well.

With reference to the remaining figures, the MRI-based ring electrode switching systems and methods will be explained in greater detail with reference to various illustrative examples.

Leads With Ring Switching Elements to Reduce MRI-Induced Heating

FIG. 2 illustrates an implantable system 100 having a pacer/ICD or other implantable medical device 102 with a bipolar coaxial lead 104. The bipolar lead includes a tip electrode 106 connected to the pacer/ICD via a tip conductor 108 coupled to a tip connector or terminal 110 of the pacer/ICD. The bipolar lead also includes a ring electrode 107 connected to the pacer/ICD via a ring conductor 109 coupled to a ring connector or terminal 111 of the pacer/ICD. Depending upon the particular implementation, during pacing/sensing, the tip electrode may be more negative than the ring, or vice versa. A conducting path 112 between the tip electrode 106 to the ring electrode 107 is provided through patient tissue (typically cardiac tissue.) A ring switch or other ring switching element 116 is positioned along conductor 109 at a distal portion thereof near the ring electrode 107, principally to reduce tip heating, though it also helps to reduce any ring heating. The ring switch is controlled by a control line 114 (which, depending upon the implementation of the switch, may include one or more individual control lines). That is, the pacer/ICD includes an MRI/RF sensor 117 for detecting MRI fields and/or strong REF fields and a switch controller 118, which operates in response to signals received from the sensor. In particular, the switch controller sends a signal to the ring switch to open the switch while MRI fields or other fields having strong RF components are present. The ring switch remains closed otherwise. As shown, the pacer/ICD also includes a pulse generator 120 for generating therapeutic pacing pulses for delivery to patient tissue via the tip and ring electrodes while the ring switch is closed, in accordance with otherwise conventional pacing techniques. Note that the pacer/ICD may include a wide variety of other components for controlling pacing/sensing/shocking (examples of which are discussed below with reference to FIG. 13.)

Insofar as the MRI/RF sensor is concerned, depending upon the implementation, the sensor may be configured to sense the strong magnetic fields of the MRI (such as the strong pulsed gradient fields) or the sensor may instead be configured to sense strong RF fields arising from any source, or both. That is, the sensor need not be limited to just sensing MRI fields but may additionally or alternatively respond to any electromagnetic fields having RF components. Hence, generally speaking, a sensor is provided for detecting the presence of electromagnetic fields sufficient to induce significant lead heating. Control circuitry is provided for generating control signals for controlling the switch of the lead so as to open the switch in the presence of the fields and to close the switch otherwise. Suitable threshold values may be set in advance to distinguish between low intensity MRI and/or RF fields (that do not present any risk of significant lead heating) from more intense MRI and/or RF fields (that do present a risk of significant lead heating). Routine experimentation may be employed to identify suitable thresholds.

To sense magnetic fields, a magnetometer or other suitable device may be employed. Devices specifically designed to sense pulsed gradient magnetic fields could be used. See, e.g., the above-cited patent to Kroll et al. (U.S. Pat. No. 7,369, 898). To sense RF fields, otherwise conventional RF field sensing devices may be employed. Note that the RF shielding aspects of the invention principally operate to reduce heating due to the RF fields of the MRI as the RF fields present the most significant source of lead heating. Hence, it is typically sufficient to detect and respond to strong RF fields. That is, as already noted, the switch controller may be configured so as to open the ring switch in the presence of strong RF fields, regardless of whether or not pulsed gradient magnetic fields are also present. However, the pulsed gradient fields can also cause problems and so disconnection of the ring switch in the presence of strong pulsed gradient magnetic fields is also helpful. Since MRI fields include both strong pulsed gradient magnetic fields and strong RF fields, it is often sufficient to just detect the strong magnetic fields of the MRI using a magnetometer and to open the ring switch accordingly, without further distinguishing among the various fields and their separate effects.

In any case, with the coaxial lead arrangement of FIG. 2, during an MRI, a current loop might be induced within the lead (and within circuit components within the pacer/ICD that electrically connect terminals 110 and 111) if the switch were closed during the MRI or if no switch were present. Without the open switching element, the current loop might pass through patient tissue from the tip electrode to the ring electrode before returning to the pacer/ICD, causing considerable resistive heating at the tip electrode and in the intervening tissue. As explained above, such heating can damage patient tissue and interfere with pacing and sensing. With switch 116 held open, however, no current loop can pass through the switch, thereby blocking a significant source of tip heating. Note, though, that current loops might potentially still be induced that pass from the tip electrode to the housing of the pacer/ICD or to other electrodes within the lead system, such as the tip electrodes of other nearby leads. However, by disconnecting ring electrode 107 from outer, ring conductor 109 of the coaxial lead at the distal end of the ring conductor, the ring conductor thereby acts as an RF shield to shield a large portion of the inner, tip conductor, thus reducing the likelihood of currents being induced via the tip conductor, the tip electrode, and other electrodes of the implanted system. This is illustrated more clearly in FIGS. 3 and 4.

FIG. 3 illustrates a portion of bipolar lead 104, particularly illustrating the locations of tip electrode 106, ring electrode 107 and ring switch 116, as well as the coaxial configuration of the tip and ring conductors 108 and 109. Ring conductor 109 surrounds tip conductor 108 and separated therefrom by an insulator 122. An exterior surface of ring conductor 109 is covered by or coated by another insulator 124. A connection line 114 is shown (within the cross-sectional view) within the inner insulator for routing control signals between switch 116 and the switch controller of the pacer/ICD (FIG. 2). With this arrangement, when switch 116 is opened, ring conductor 109 is electrically isolated from patient tissue. Since the ring conductor extends the length of the lead from ring electrode to the header of the lead (not specifically shown in FIGS. 2 and 3), the ring conductor thereby covers a substantial portion of the inner tip conductor 108 and acts as an RF shield to those portions of the tip conductor during an MRI procedure. Hence, any currents that would otherwise be induced along the tip conductor by the RF fields of the MRI are substantially reduced.

Depending upon the particular implementation, the RF shielding provided by ring conductor 109 may be sufficient to reduce induced currents along tip conductor 108 by an amount sufficient to prevent any significant tip heating, such that a separate tip disconnect switch is not needed. In other implementations, to be discussed below, the RF shielding provided by the ring conductor is at least sufficient to reduce the induced voltages within tip conductor to permit the use of a physically smaller and less robust disconnect switch along the tip conductor (see FIG. 9).

In one particular example, the ring switching 116 is configured as a mechanical switch controlled by electronics or control circuit in device, multi-value resistors, transistors/microelectromechanical systems (MEMS), etc. The particular switch to be used may be chosen, at least in part, based on the amount of voltage expected to be induced within the lead during an MRI, which may depend upon the location and orientation of the lead within the patient relative to the pacer/ICD and on the distance between the tip and ring electrodes and the impedance of tissues therebetween. In this regard, a switching element should be chosen for use as the ring switch that presents a sufficiently high breakdown voltage such that the voltages induced by the MRI do not break down the switch.

Figure 4A:
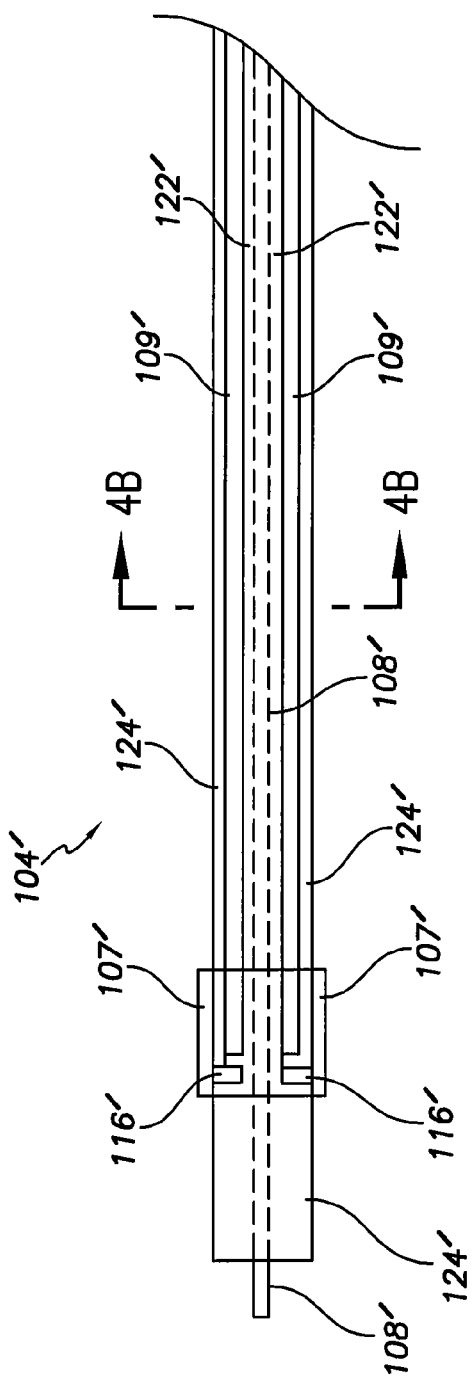
FIG. 4 includes another elevation view of a portion of the bipolar lead of FIG. 2 and also a cross-sectional view.
Figure 4B:
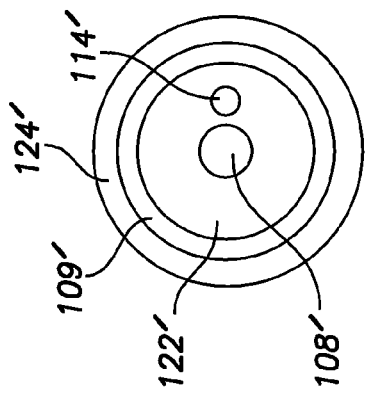

FIG. 4 illustrates a portion of an alternative implementation of a bipolar lead 104', again illustrating the locations of various components such as tip electrode 106', ring electrode 107' and ring switch 116', as well as the coaxial configuration of the tip and ring conductors 108' and 109'. Ring conductor 109' again surrounds tip conductor 108' and is separated therefrom by an insulator 122'. An exterior surface of ring conductor 109' is covered by or coated by another insulator 124'. A connection line 114' is shown within the inner insulator (within the cross-sectional view) for routing control signals. An electronic switching circuit 116' is interposed between the ring electrode 107' and a distal end of the ring conductor 109'. In the arrangement shown, switch 116' is "open" such that there is a gap between the end of the ring conductor and the inner surface of the ring electrode, electrically isolating one from the other. When the switch is closed (not shown), switch 116' instead electrically connects the end of the ring conductor and the inner surface of the ring electrode. In one example, a MEMS switch is employed to selectively connect the ring electrode and ring conductor. As noted, however, a wide variety of switches, switching circuits, switching elements, and other means for switching may be employed.

FIGS. 5 and 6 illustrate an alternative implantable medical system 200 wherein the ring electrode switch is mounted within a header 201 of a bipolar coaxial lead 204, which is connected to a pacer/ICD 202. Again, the bipolar lead includes a tip electrode 206 connected to the pacer/ICD via a tip conductor 208, which is in turn coupled to a tip terminal 210 of the pacer/ICD. The bipolar lead also includes ring electrode 207 connected via ring conductor 209 coupled to ring terminal 211. A conducting path 212 is provided through patient tissue from the tip electrode to the ring electrode. The ring switch 216 is positioned at or near a proximal end of conductor 209 within header 201. The ring switch is controlled by a control line 214 (which, again, may include one, two or more separate control lines depending upon the implementation of the switch). The pacer/ICD includes an MRI/RF sensor 217 for detecting MRI fields and a switch controller 218 that operates to open the switch while MRI fields or other strong RF fields are present and to close the switch otherwise. The pacer/ICD also includes a pulse generator 220 for generating therapeutic pacing pulses for delivery to patient tissue via the lead while the ring switch is closed. As with the arrangement of FIGS. 2-4, during an MRI or in the presence of other strong RF fields, no current loop can pass through the switching element, thereby reducing tip heating. Also, ring conductor 209 acts as an RF shield to shield a large portion of the inner, tip conductor, thus reducing the likelihood of currents being induced via the tip conductor, the tip electrode, and other electrodes of the implanted system. This is illustrated more clearly in FIG. 6.

FIG. 6 illustrates a portion of bipolar lead 204, particularly illustrating the locations of tip electrode 206, ring electrode 207 and ring switch 216, as well as the coaxial configuration of the tip and ring conductors 208 and 209. Ring conductor 209 surrounds tip conductor 208 and is separated therefrom by an insulator 222. An exterior surface of ring conductor 209 is covered by insulator 224. With this arrangement, when switch 216 is opened, ring conductor 209 remains electrically connected to patient tissue at electrode 207 but electrically isolated from the pacer/ICD. The ring conductor again acts as an RF shield to shield those portions of the tip conductor that it encloses during an MRI procedure. Hence, any currents that would otherwise be induced along the tip conductor by the RF components of the MRI are substantially reduced. Again, depending upon the particular implementation, the RF shielding provided by ring conductor 209 may be sufficient to reduce induced currents along tip conductor 208 by an amount sufficient to prevent any significant tip heating, such that a separate tip disconnect switch is not needed. In other implementations, the RF shielding provided by the ring conductor is at least sufficient to reduce the intensity of induced voltages within tip conductor to permit the use of a physically smaller and less robust disconnect switch along the tip conductor.

Figure 7:
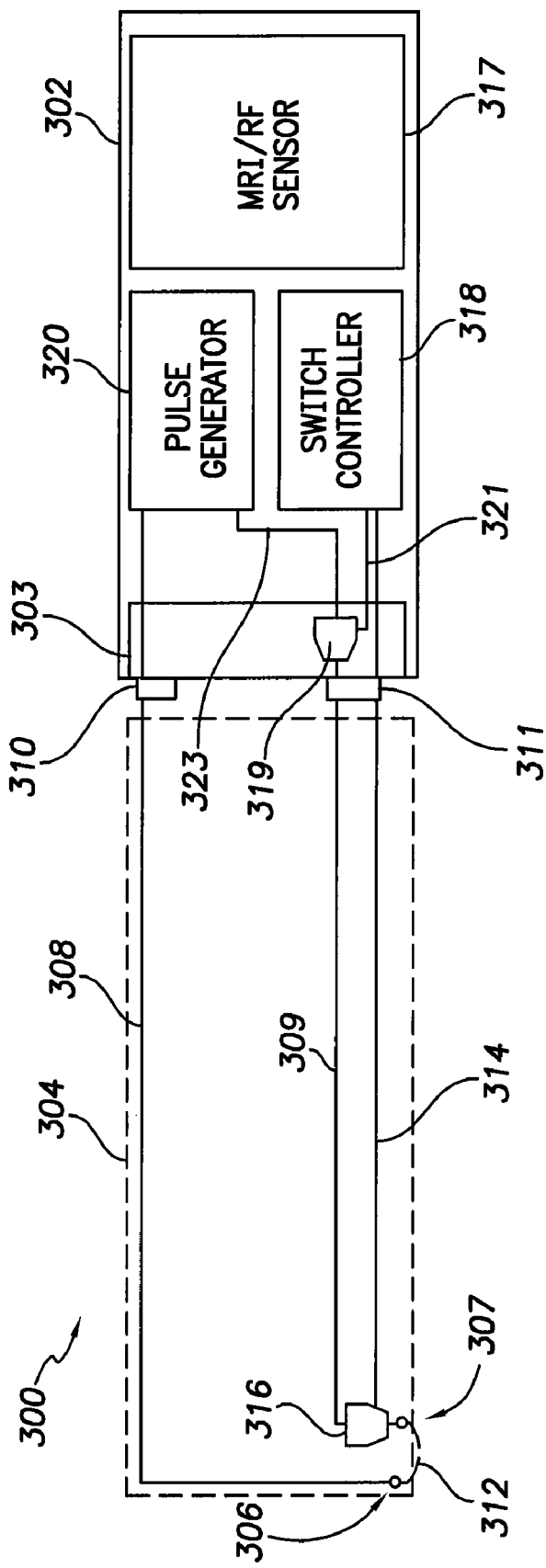
FIG. 7 is an elevational view of a portion of yet another alternative bipolar lead to that of FIG. 2, particularly illustrating the placement of a ring electrode switching element in the feed-through of the pacer/ICD.
Figure 8:
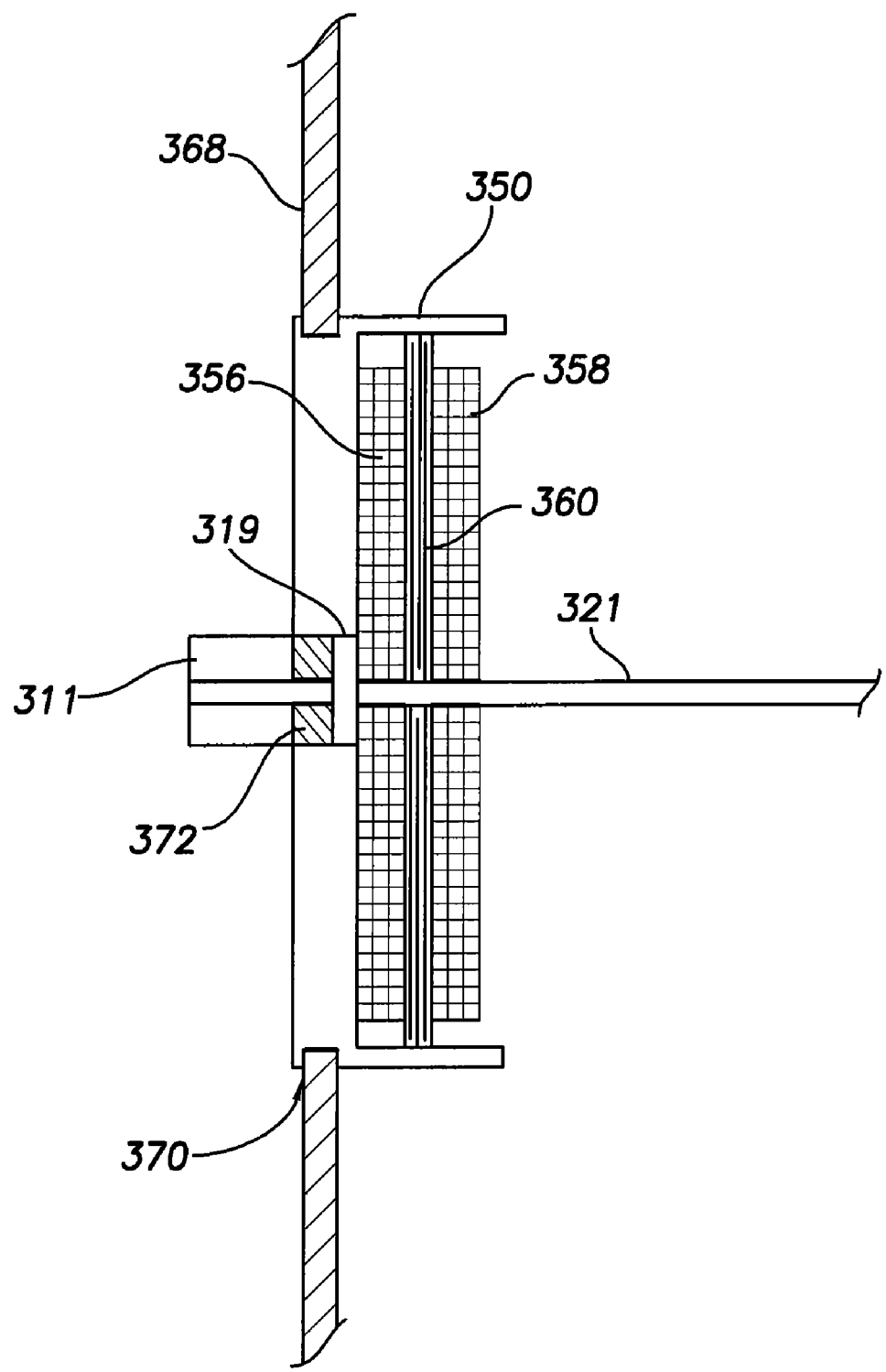
FIG. 8 is a cross-sectional view of the feed-through of the pacer/ICD of FIG. 7, particularly illustrating the placement of a ring electrode switching element in the feed-through of the pacer/ICD.

FIGS. 7 and 8 illustrate an alternative implantable medical system 300 wherein a ring electrode switch is mounted within a feed-through 303 portion of a pacer/ICD 310. A bipolar coaxial lead 304, configured as described above with reference to FIGS. 2-4, is connected to a pacer/ICD 302.

Again, the bipolar lead includes a tip electrode 306 connected to the pacer/ICD via a tip conductor 308, which is in turn coupled to a tip terminal 310 of the pacer/ICD. The bipolar lead also includes ring electrode 307 connected via ring conductor 309 coupled to ring terminal 311. A conducting path 312 is provided through patient tissue from the tip electrode to the ring electrode. A first ring switch 316 is positioned at or near a proximal end of conductor 309 within header 301. Ring switch 316 is controlled by a control line 314. A second ring switch 319 is positioned within a feed-through portion 303 of the pacer/ICD between a pulse generator 320 and ring terminal 311 along line 323. Ring switch 319 is controlled by a control line 321. The pacer/ICD includes an MRI/RF sensor 317 for detecting MRI fields (and/or other strong RF fields) and a switch controller 318 that operates to open the two switches while the fields are present and to close the two switches otherwise. The pulse generator generates therapeutic pacing pulses for delivery to patient tissue via the lead while the two ring switches is closed.

The placement of switch 319 within feed-through 303 is more clearly illustrated within FIG. 8. In the example shown therein, the feed-through includes a T-type filter 350, i.e. a filter having an inductor-capacitor-inductor (LCL) design. Filter 350 includes a pair of inductors 356 and 358 with a capacitor 310 mounted therebetween. Filter 350 is connected along input/output signal line 321 between ring terminal 311 and the internal circuitry of the device (e.g. pulse generator 320). These and other feed-through designs are discussed in, e.g., U.S. patent application Ser. No. 11/450,945, filed Jun. 9, 2006, of Propato, entitled "Multilayer L-section Filter for use in an Implantable Medical Device," now abandoned. Switch 317 is mounted along line 321 between feed-through filter 350 and an inner side of the device housing 368. The signal line 321 also passes through an insulator 372 (the external lead is not shown in the figure). The mechanical interface between insulator 372 and the signal line 321 along with the entire feed-through filter case 350 is welded to the device housing at perimeter 370 to provide a hermetic seal. Close mounting of the components of the T-type filter to the feed-through port helps prevent high frequency signals from propagating into the device housing. This is just one exemplary physical embodiment of a feed-through; numerous other embodiments may be employed as well.

Returning to FIG. 7, as with the arrangements discussed above, during an MRI, no current loop can pass through the two switches, thereby reducing lead heating. Also, ring conductor 309 acts as an RF shield to shield a large portion of the inner, tip conductor, thus reducing the likelihood of currents being induced via the tip conductor, the tip electrode, and other electrodes of the implanted system. Indeed, with this arrangement, when switches 316 and 319 are opened, ring conductor 309 is electrically disconnected from both the patient tissue (at electrode 307) and from the internal components of the pacer/ICD (such as pulse generator 320). The ring conductor thus acts as an RF shield to those portions of the tip conductor that it encloses during an MRI procedure. Hence, any currents that would otherwise be induced along the tip conductor by the electromagnetic fields of the MRI are substantially reduced. Again, depending upon the particular implementation, the RF shielding provided by ring conductor 309 may be sufficient to reduce induced currents along tip conductor 308 by an amount sufficient to prevent any significant tip heating, such that a separate tip disconnect switch is not needed. In other implementations, the RF shielding provided by the ring conductor is at least sufficient to reduce the induced voltages within tip conductor to permit the use of a physically smaller and less robust disconnect switch along the tip conductor. Also, note that the second switch may instead by provided within the header of the lead, as shown in FIGS. 5 and 6.

Figure 9:
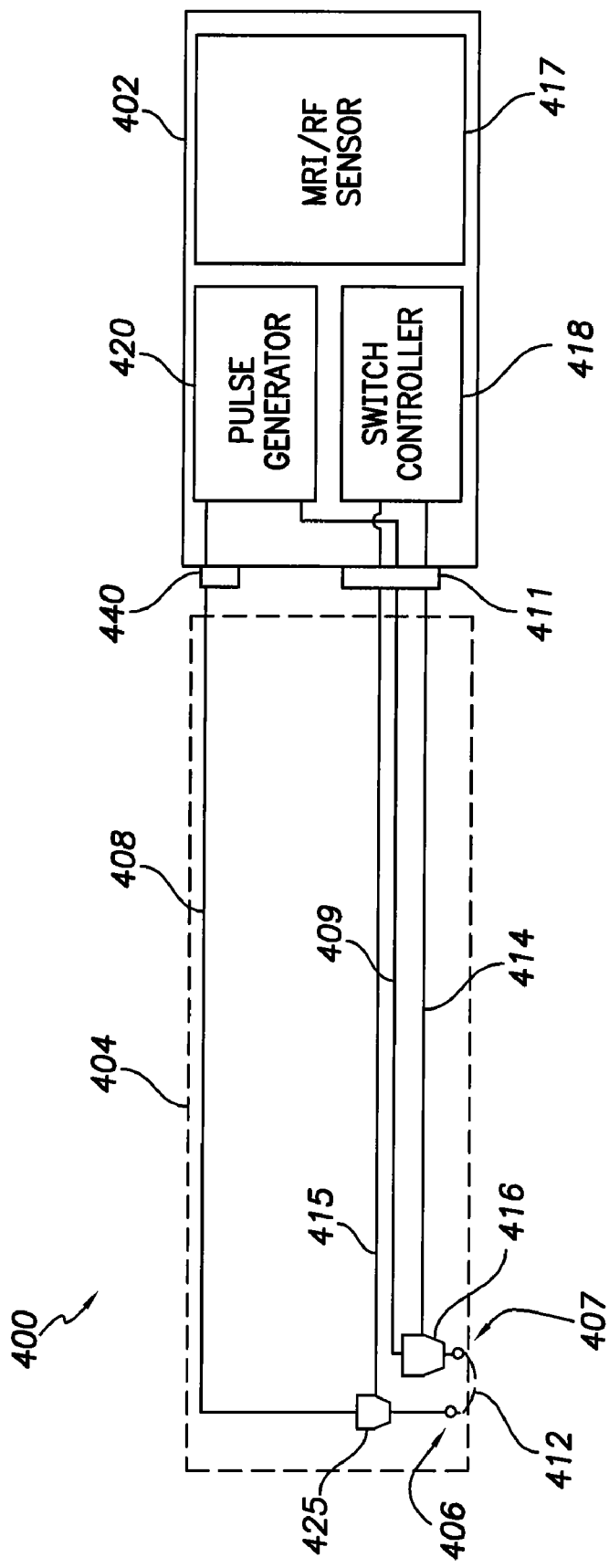
FIG. 9 is an elevational view of a portion of still yet another alternative bipolar lead to that of FIG. 2, particularly illustrating the placement of a switching element near both the tip and ring electrodes.

FIG. 9 illustrates an arrangement wherein both tip and ring switches are provided within a coaxial bipolar lead. This arrangement is similar to that of FIG. 2 (except for the addition of the tip switch) and hence will only briefly be summarized. Implantable system 400 includes a pacer/ICD 402 with a bipolar coaxial lead 404 having a tip electrode 406 and a tip conductor 408 coupled to the pacer/ICD via a tip terminal 410 ICD. The bipolar lead also includes a ring electrode 407 and a ring conductor 409 coupled to the pacer/ICD via a ring terminal 411. A conducting path 412 is provided through patient tissue between the tip electrode 406 to the ring electrode 407. A ring switch or other ring switching element 416 is positioned along conductor 409 at a distal portion thereof near the ring electrode 407. A tip switch or other tip switching element 425 is positioned along conductor 408 at a distal portion thereof near the tip electrode 406.

The tip and ring switches are controlled by control lines 414, 415 (respectively) to disconnect the switches during MRI procedures. That is, the pacer/ICD again includes an MRI/RF sensor 417 and a switch controller 418, which sends signals to the tip and ring switches to open the switches while MRI fields or other fields having strong RF components are present. The tip and ring switches remain closed otherwise. The pacer/ICD also includes a pulse generator 420 for generating therapeutic pacing pulses for delivery to patient tissue via the tip and ring electrodes while the tip and ring switches are closed, in accordance with otherwise conventional pacing techniques.

As with the implementations discussed above, during an MRI, the ring conductor acts as an RF shield to shield a large portion of the inner, tip conductor, thus permitting the use of a smaller and less robust tip switch than might otherwise be required (as illustrated by way of the smaller tip switch size within FIG. 9). For example, a switch with a lower breakdown voltage might be employed as the tip switch. This is advantageous since the tip switch is located near the tip electrode in a narrow portion of the lead where there is little room for placement of a large, robust switch. Again, otherwise routine testing and experimentation may be performed to determine the appropriate switches for use in a particular lead for use in a particular patient so as to achieve adequate reduction in lead temperatures during MRIs within the patient.

Figure 10:
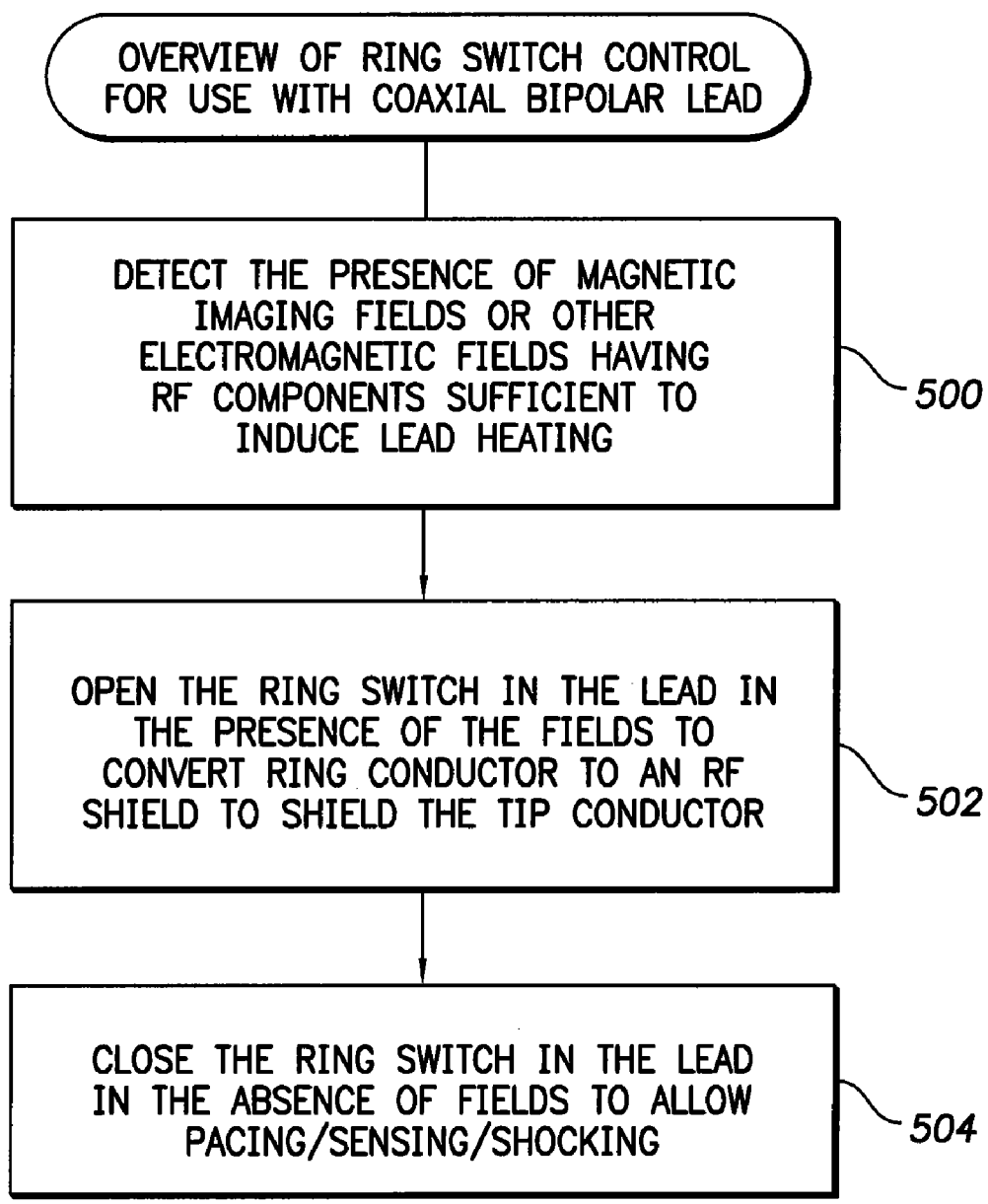
FIG. 10 is a flow diagram summarizing techniques for use in operating the switch-based bipolar leads of FIGS. 2-9.

FIG. 10 broadly summarizes the above-described switching techniques. At step 500, the pacer/ICD detects the presence of magnetic imaging fields or other electromagnetic fields having RF components sufficient to induce lead heating using a magnetometer or other suitable sensing device. At step 502, the pacer/ICD opens the ring switch in the lead in the presence of the fields to convert the ring conductor to an RF shield to shield the tip conductor and thereby reduce the likelihood of induce currents and lead heating. At step 504, the pacer/ICD closes the ring switch in the lead in the absence of the fields to allow pacing, sensing and shocking.

Leads With Band Stop Filter Elements to Reduce MRI-Induced Heating

Figure 11:
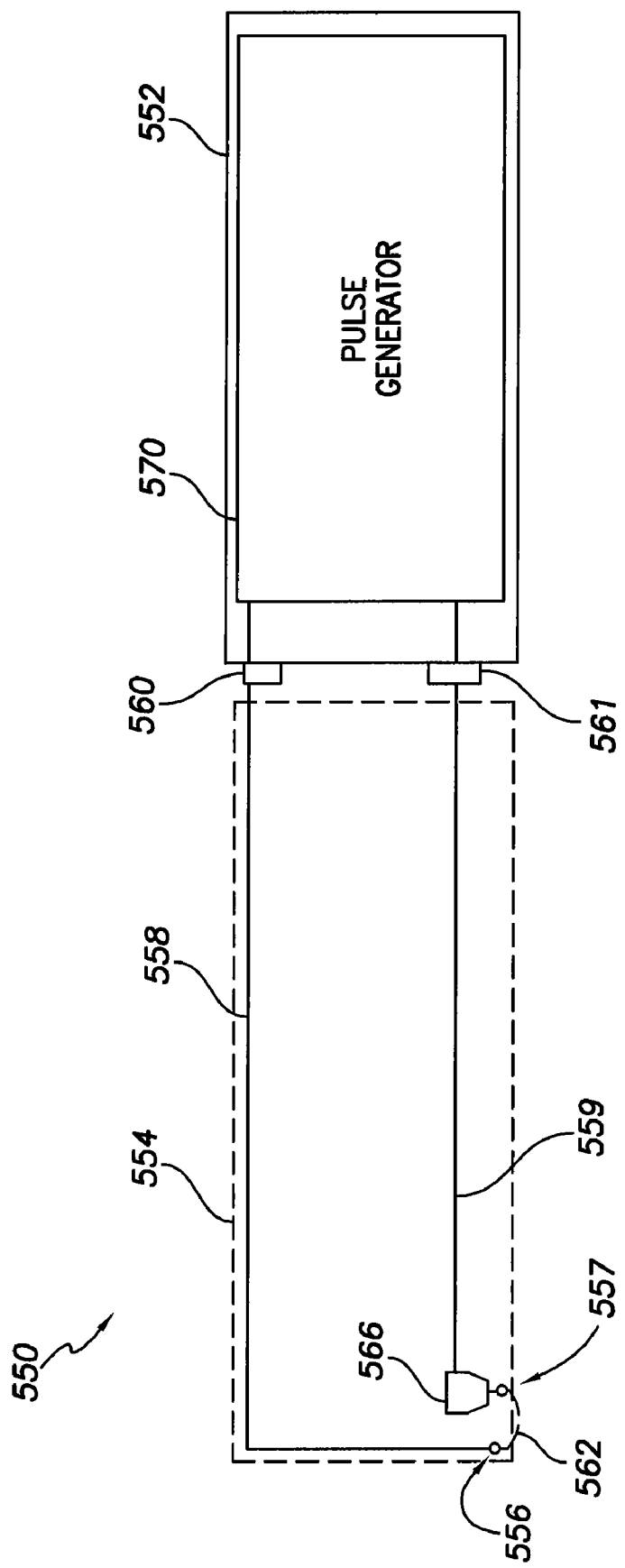
FIG. 11 is a block diagram, partly in schematic form, illustrating a bipolar lead for use with the pacer/ICD of FIG. 1 wherein a band stop filter is mounted to the lead near the ring electrode.

FIG. 11 illustrates a band stop filter implementation. This implementation is similar to the switch implementation of FIG. 2 and hence only pertinent differences will be described in any detail. Briefly, an implantable system 550 includes a pacer/ICD or other implantable medical device 552 and a bipolar coaxial lead 554. The bipolar lead includes a tip electrode 556 connected via a tip conductor 558 to a tip connector or terminal 560 of the pacer/ICD. The bipolar lead also includes a ring electrode 557 connected via a ring conductor 559 to a ring connector or terminal 561 of the pacer/ICD. A conducting path 562 between the tip electrode 556 to the ring electrode 557 is provided through patient tissue. A band stop filter or other band stop filtering element 566 is positioned along conductor 559 at a distal portion thereof near the ring electrode 557. The band stop filter is provided to block signals at the RF frequencies of MRI fields. The filter may be configured, e.g., with self-resonant frequencies at RF of MRI: 63.7 MHz±0.345 MHz for 1.5 T or 125.6±3.5 MHz for 3T. The filter may be implemented using any suitable technology such as coil inductors, integrated circuit (IC) inductors (i.e. printed traces on multi-layers), LC resonant tanks, etc.

As shown, the pacer/ICD includes a pulse generator 570 for generating therapeutic pacing pulses for delivery to patient tissue via the tip and ring electrodes in accordance with otherwise conventional pacing techniques when MRI fields are not present. During an MRI, a current loop might be induced within the lead if the band stop filter were not present. Without the band stop filter, the current loop might pass through patient tissue from the tip electrode to the ring electrode before returning to the pacer/ICD, causing considerable resistive heating at the tip electrode and in the intervening tissue. With the band stop filter, however, no RF current loops can pass through the band stop filter, thereby blocking a significant source of tip heating. Moreover, at RF frequencies, the ring conductor acts as an RF shield to shield a large portion of the inner, tip conductor, thus reducing the likelihood of currents being induced via the tip conductor, the tip electrode, and other electrodes of the implanted system.

The various systems and methods described above can be exploited for use with a wide variety of implantable medical systems. For the sake of completeness, a detailed description of an exemplary pacer/ICD and lead system will now be provided.

Exemplary Pacer/ICD/Lead System

FIG. 12 provides a simplified diagram of the pacer/ICD of FIG. 1, which is a dual-chamber stimulation device capable of treating both fast and slow arrhythmias with stimulation therapy, including cardioversion, defibrillation, and pacing stimulation. To provide atrial chamber pacing stimulation and sensing, pacer/ICD 10 is shown in electrical communication with a heart 612 by way of a left atrial lead 620 having an atrial tip electrode 622 and an atrial ring electrode 623 implanted in the atrial appendage. Pacer/ICD 10 is also in electrical communication with the heart by way of a right ventricular lead 630 having, in this embodiment, a ventricular tip electrode 632, a right ventricular ring electrode 634, a right ventricular (RV) coil electrode 636, and a superior vena cava (SVC) coil electrode 638. Typically, the right ventricular lead 630 is transvenously inserted into the heart so as to place the RV coil electrode 636 in the right ventricular apex, and the SVC coil electrode 638 in the superior vena cava. Accordingly, the right ventricular lead is capable of receiving cardiac signals, and delivering stimulation in the form of pacing and shock therapy to the right ventricle. A ring switch 616, configured as described above, is positioned near ring electrode 634. In the figure, the ring switch is shown in phantom lines, as it is internal to the lead. Alternatively, switch 616 may be a band pass filter.

To sense left atrial and ventricular cardiac signals and to provide left chamber pacing therapy, pacer/ICD 10 is coupled to a "coronary sinus" lead 624 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 624 is designed to receive atrial and ventricular cardiac signals and to deliver left ventricular pacing therapy using at least a left ventricular tip electrode 626, left atrial pacing therapy using at least a left atrial ring electrode 627, and shocking therapy using at least a left atrial coil electrode 628. With this configuration, biventricular pacing can be performed. Although only three leads are shown in FIG. 12, it should also be understood that additional stimulation leads (with one or more pacing, sensing and/or shocking electrodes) may be used in order to efficiently and effectively provide pacing stimulation to the left side of the heart or atrial cardioversion and/or defibrillation. Also, additional ring switches or filters may be installed in the various leads, as already explained, such as in the LV/CS lead or the RA lead. Ring switches or filters may be installed at other locations within the leads, such as within lead headers 629. Also, tip switches may be installed.

Figure 13:
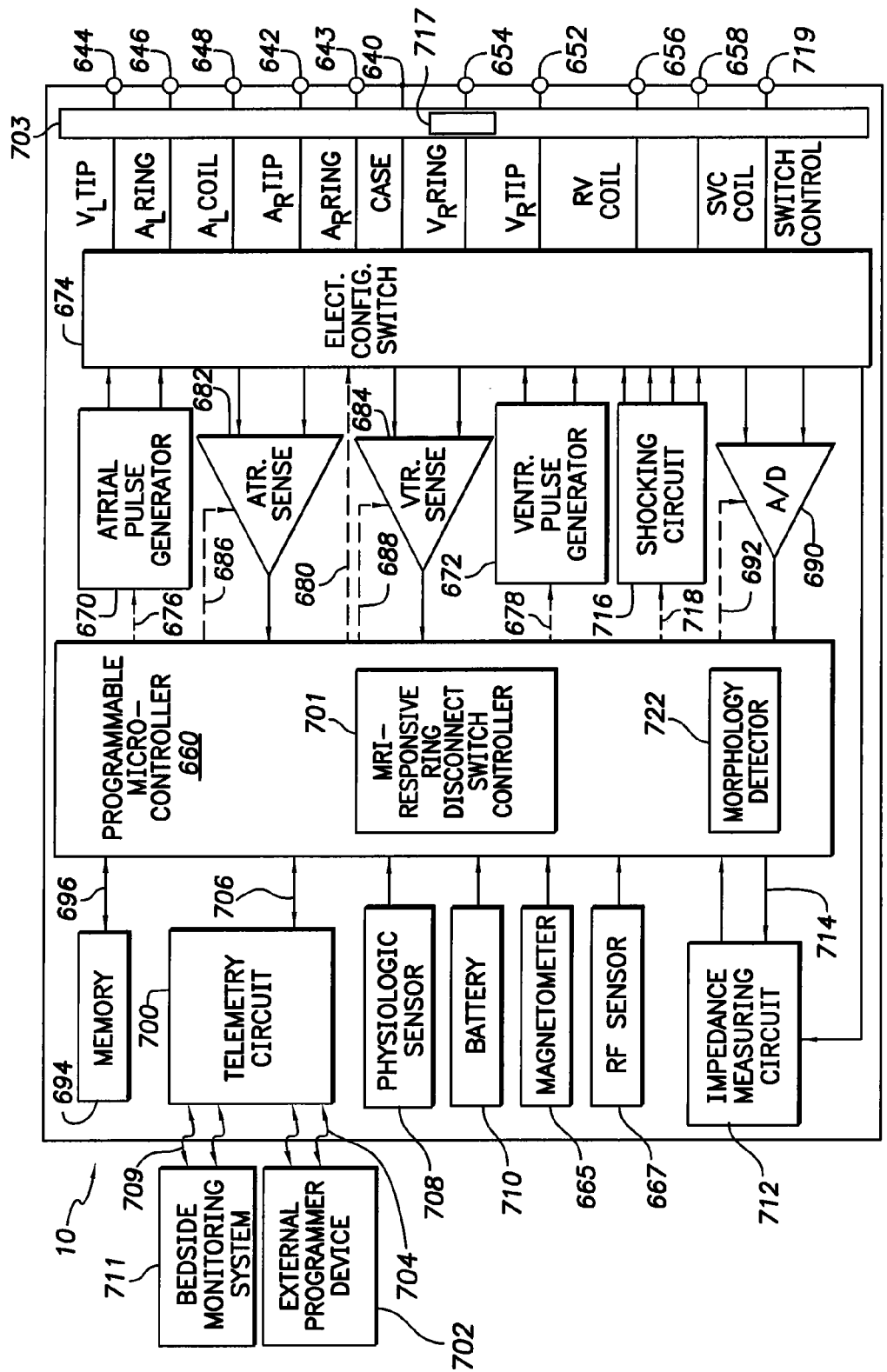
FIG. 13 is a functional block diagram of the pacer/ICD of FIG. 12, illustrating basic circuit elements that provide cardioversion, defibrillation and/or pacing stimulation in four chambers of the heart, as well as an MRI-responsive switching controller.

A simplified block diagram of internal components of pacer/ICD 10 is shown in FIG. 13. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy.

The housing 640 for pacer/ICD 10, shown schematically in FIG. 13, is often referred to as the "can", "case" or "case electrode" and may be programmably selected to act as the return electrode for all "unipolar" modes. The housing 640 may further be used as a return electrode alone or in combination with one or more of the coil electrodes, 628, 636 and 638, for shocking purposes. The housing 640 further includes a connector (not shown) having a plurality of terminals, 642, 643, 644, 646, 648, 652, 654, 656 and 658 (shown schematically and, for convenience, the names of the electrodes to which they are connected are shown next to the terminals). As such, to achieve right atrial sensing and pacing, the connector includes at least a right atrial tip terminal ($A_R$ TIP) 642 adapted for connection to the atrial tip electrode 622 and a right atrial ring ($A_R$ RING) electrode 643 adapted for connection to right atrial ring electrode 623. To achieve left chamber sensing, pacing and shocking, the connector includes at least a left ventricular tip terminal ($V_L$ TIP) 644, a left atrial ring terminal ($A_L$ RING) 646, and a left atrial shocking terminal ($A_L$ COIL) 648, which are adapted for connection to the left ventricular ring electrode 626, the left atrial tip electrode 627, and the left atrial coil electrode 628, respectively. To support right chamber sensing, pacing and shocking, the connector further includes a right ventricular tip terminal ($V_R$ TIP) 652, a right ventricular ring terminal ($V_R$ RING) 654, a right ventricular shocking terminal ($R_V$ COIL) 656, and an SVC shocking terminal (SVC COIL) 658, which are adapted for connection to the right ventricular tip electrode 632, right ventricular ring electrode 634, the RV coil electrode 636, and the SVC coil electrode 638, respectively. A feed-through is shown schematically via block 703. A ring switch 717 is shown as a component of the feed-through, as discussed above with reference to FIGS. 7 and 8. As already explained, ring switches may be provided within the feed-through, within the lead, or both. For controlling the ring switch 616 within the RV lead, a switch terminal 719 is provided.

At the core of pacer/ICD 10 is a programmable microcontroller 660, which controls the various modes of stimulation therapy. As is well known in the art, the microcontroller 660 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 660 includes the ability to process or monitor input signals (data) as controlled by a program code stored in a designated block of memory. The details of the design and operation of the microcontroller 660 are not critical to the invention. Rather, any suitable microcontroller 660 may be used that carries out the functions described herein. The use of microprocessor-based control circuits for performing timing and data analysis functions are well known in the art.

As shown in FIG. 13, an atrial pulse generator 670 and a ventricular pulse generator 672 generate pacing stimulation pulses for delivery by the right atrial lead 620, the right ventricular lead 630, and/or the coronary sinus lead 624 via an electrode configuration switch 674. It is understood that in order to provide stimulation therapy in each of the four chambers of the heart, the atrial and ventricular pulse generators, 670 and 672, may include dedicated, independent pulse generators, multiplexed pulse generators or shared pulse generators. The pulse generators, 670 and 672, are controlled by the microcontroller 660 via appropriate control signals, 676 and 678, respectively, to trigger or inhibit the stimulation pulses.

The microcontroller 660 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 674 includes a plurality of switches for connecting the desired electrodes to the appropriate I/O circuits, thereby providing complete electrode programmability. Accordingly, the switch 674, in response to a control signal 680 from the microcontroller 660, determines the polarity of the stimulation pulses (e.g., unipolar, bipolar, combipolar, etc.) by selectively closing the appropriate combination of switches (not shown) as is known in the art.

Atrial sensing circuits 682 and ventricular sensing circuits 684 may also be selectively coupled to the right atrial lead 620, coronary sinus lead 624, and the right ventricular lead 630, through the switch 674 for detecting the presence of cardiac activity in each of the four chambers of the heart. Accordingly, the atrial (ATR. SENSE) and ventricular (VTR. SENSE) sensing circuits, 682 and 684, may include dedicated sense amplifiers, multiplexed amplifiers or shared amplifiers. The switch 674 determines the "sensing polarity" of the cardiac signal by selectively closing the appropriate switches, as is also known in the art. In this way, the clinician may program the sensing polarity independent of the stimulation polarity. Each sensing circuit, 682 and 684, preferably employs one or more low power, precision amplifiers with programmable gain and/or automatic gain control and/or automatic sensitivity control, bandpass filtering, and a threshold detection circuit, as known in the art, to selectively sense the cardiac signal of interest. The automatic gain and/or sensitivity control enables pacer/ICD 10 to deal effectively with the difficult problem of sensing the low amplitude signal characteristics of atrial or ventricular fibrillation. The outputs of the atrial and ventricular sensing circuits, 682 and 684, are connected to the microcontroller 660 which, in turn, are able to trigger or inhibit the atrial and ventricular pulse generators, 670 and 672, respectively, in a demand fashion in response to the absence or presence of cardiac activity in the appropriate chambers of the heart.

For arrhythmia detection, pacer/ICD 10 utilizes the atrial and ventricular sensing circuits, 682 and 684, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 660 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 690. The data acquisition system 690 is configured to acquire intracardiac electrogram signals, convert the raw analog data into a digital signal, and store the digital signals for later processing and/or telemetric transmission to an external device 702. The data acquisition system 690 is coupled to the right atrial lead 620, the coronary sinus lead 624, and the right ventricular lead 630 through the switch 674 to sample cardiac signals across any pair of desired electrodes. The microcontroller 660 is further coupled to a memory 694 by a suitable data/address bus 696, wherein the programmable operating parameters used by the microcontroller 660 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 694 through a telemetry circuit 700 in telemetric communication with an external device 702, such as a programmer, transtelephonic transceiver or a diagnostic system analyzer, or a bedside monitoring system 711. The telemetry circuit 700 is activated by the microcontroller by a control signal 706. The telemetry circuit 700 advantageously allows IEGMs and other electrophysiological signals and/or hemodynamic signals and status information relating to the operation of pacer/ICD 10 (as stored in the microcontroller 660 or memory 694) to be sent to the external programmer device 702 through an established communication link 704 or to a separate bedside monitor via link 709.

Pacer/ICD 10 further includes an accelerometer or other physiologic sensor 708, commonly referred to as a "rate-responsive" sensor because it is typically used to adjust pacing stimulation rate according to the exercise state of the patient. However, the physiological sensor 708 may further be used to detect changes in cardiac output, changes in the physiological condition of the heart, or diurnal changes in activity (e.g., detecting sleep and wake states) and to detect arousal from sleep. Accordingly, the microcontroller 660 responds by adjusting the various pacing parameters (such as rate, AV Delay, V-V Delay, etc.) at which the atrial and ventricular pulse generators, 670 and 672, generate stimulation pulses. While shown as being included within pacer/ICD 10, it is to be understood that the physiologic sensor 708 may also be external to pacer/ICD 10, yet still be implanted within or carried by the patient. A common type of rate responsive sensor is an activity sensor incorporating an accelerometer or a piezoelectric crystal, which is mounted within the housing 640 of pacer/ICD 10. Other types of physiologic sensors are also known, for example, sensors that sense the oxygen content of blood, respiration rate and/or minute ventilation, pH of blood, ventricular gradient, etc. A magnetometer 665 is provided for sensing magnetic fields associated with MRI procedures. An RF sensor 667 is provided for sensing RF fields associated with MRI procedures or arising from other sources. The two sensing components need not both be provided.

The pacer/ICD additionally includes a battery 710, which provides operating power to all of the circuits shown in FIG. 13. The battery 710 may vary depending on the capabilities of pacer/ICD 10. If the system only provides low voltage therapy, a lithium iodine or lithium copper fluoride cell may be utilized. For pacer/ICD 10, which employs shocking therapy, the battery 710 must be capable of operating at low current drains for long periods, and then be capable of providing high-current pulses (for capacitor charging) when the patient requires a shock pulse. The battery 710 must also have a predictable discharge characteristic so that elective replacement time can be detected. Accordingly, pacer/ICD 10 is preferably capable of high voltage therapy and appropriate batteries.

As further shown in FIG. 13, pacer/ICD 10 is shown as having an impedance measuring circuit 712 which is enabled by the microcontroller 660 via a control signal 714. Various uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, measuring lead resistance, etc. The impedance measuring circuit 120 is advantageously coupled to the switch 74 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 660 further controls a shocking circuit 716 by way of a control signal 718. The shocking circuit 716 generates shocking pulses of low (up to 0.5 joules), moderate (0.5-11 joules) or high energy (11 to 40 joules), as controlled by the microcontroller 660. Such shocking pulses are applied to the heart of the patient through at least two shocking electrodes, and as shown in this embodiment, selected from the left atrial coil electrode 628, the RV coil electrode 636, and/or the SVC coil electrode 638. The housing 640 may act as an active electrode in combination with the RV electrode 636, or as part of a split electrical vector using the SVC coil electrode 638 or the left atrial coil electrode 628 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 11-40 joules), delivered asynchronously (since R-waves may be too disorganized), and pertaining exclusively to the treatment of fibrillation. Accordingly, the microcontroller 660 is capable of controlling the synchronous or asynchronous delivery of the shocking pulses.

Insofar as MRI-responsive control of the ring switch or other lead switches is concerned, the microcontroller has an MRI-responsive ring disconnect controller 701 that is operative to generate control signals for controlling the ring switches in response to the presence of the magnetic imaging fields or other fields having strong RF components so as to open the switch(es) in the presence of the fields and to close the switch(es) otherwise. If the lead includes band stop filters, but not switches, then a disconnect controller is not needed.

What have been described are systems and methods for use with a set of pacing/sensing leads for use with a pacer/ICD. Principles of the invention may be exploiting using other implantable systems or in accordance with other techniques. Thus, while the invention has been described with reference to particular exemplary embodiments, modifications can be made thereto without departing from the scope of the invention.

What is claimed is:

1. A lead for use with an implantable medical device for implant within a patient, the lead comprising:
   first and second electrodes for placement adjacent patient tissues;
   an inner conductor for routing signals along the lead between the first electrode and the implantable medical device;
   an outer conductor for routing signals along the lead between the second electrode and the implantable medical device;
   an insulator interposed between the outer conductor and patient tissues; and
   an electrical device connected along the outer conductor between the second electrode and the implantable medical device and operative to selectively control the conduction of signals along the outer conductor in response to the presence of particular electromagnetic fields to selectively convert the outer conductor into an electromagnetic signal shield;
   wherein the lead is a bipolar lead, wherein the first electrode is a tip electrode and the second electrode is a ring electrode, wherein the tip electrode and ring electrode are pacing and/or sensing electrodes, and wherein the inner conductor is a tip conductor and the outer conductor is a ring conductor; and
   wherein the bipolar lead is a coaxial lead wherein the tip conductor is mounted coaxially inside the ring conductor.

2. The lead of claim 1 wherein the electrical device is a switch connected along the outer conductor between the second electrode and the implantable medical device and operative to be selectively opened in response to the presence of magnetic resonance imaging (MRI) fields and closed otherwise.

3. The lead of claim 1 wherein the electrical device is a band stop filter connected along the outer conductor between the second electrode and the implantable medical device and operative to be selectively block signals having frequencies associated with magnetic resonance imaging (MRI) fields.

4. The lead of claim 1 wherein the electrical device is connected at a distal end of the outer conductor between the second electrode and the outer conductor.

5. The lead of claim 1 wherein the electrical device is connected between a distal end of the outer conductor and a connection terminal of the implantable medical device.

6. The lead of claim 5 wherein the electrical device is mounted within a header of the lead.

7. The lead of claim 1 wherein the electrical device is connected between a distal portion of the outer conductor that is coupled to the second electrode and a proximal portion of the outer conductor that is coupled to a connection terminal of the implantable medical device.

8. The lead of claim 5 wherein the electrical device is mounted within a header of the lead.

9. The lead of claim 1 wherein the insulator is mounted coaxially outside the ring conductor and extends along the lead from a distal end of the lead to the ring electrode such that the ring conductor is not in direct electrical contact with patient tissue.

10. The lead of claim 1 wherein a second insulator is provided between the coaxial tip and ring conductors.

11. The lead of claim 1 wherein the electrical device is a switch connected along the outer conductor between the second electrode and the implantable medical device and operative to be selectively opened in response to the presence of magnetic resonance imaging (MRI) fields and closed otherwise and wherein the lead further includes a control signal line for routing control signals from the implantable device to the switch for controlling the switch.

12. The lead of claim 11 wherein the control signal line is insulated from the inner and outer conductors.

* * * * *